United States Patent
Voss et al.

(10) Patent No.: US 6,176,831 B1
(45) Date of Patent: Jan. 23, 2001

(54) APPARATUS AND METHOD FOR NON-INVASIVELY MONITORING A SUBJECT'S ARTERIAL BLOOD PRESSURE

(75) Inventors: Gregory I. Voss, Solana Beach; Alvis J. Somerville; Simon E. Finburgh, both of San Diego, all of CA (US)

(73) Assignee: Tensys Medical, Inc., San Diego, CA (US)

(*) Notice: Under 35 U.S.C. 154(b), the term of this patent shall be extended for 0 days.

(21) Appl. No.: 09/120,205

(22) Filed: Jul. 20, 1998

(51) Int. Cl.$^7$ .................................................. A61B 5/00
(52) U.S. Cl. ........................ 600/485; 600/500; 600/503
(58) Field of Search ................................... 600/485, 806, 600/503

(56) References Cited

U.S. PATENT DOCUMENTS

| | | |
|---|---|---|
| 4,651,747 | 3/1987 | Link . |
| 4,771,792 | 9/1988 | Seale . |
| 4,867,170 * | 9/1989 | Takahashi ............................ 600/503 |
| 4,869,261 | 9/1989 | Penaz . |
| 4,901,733 | 2/1990 | Kaida et al. . |
| 4,924,871 | 5/1990 | Honeyager . |
| 5,119,822 | 6/1992 | Niwa . |
| 5,238,000 | 8/1993 | Niwa . |
| 5,240,007 | 8/1993 | Pytel et al. . |
| 5,273,046 | 12/1993 | Butterfield et al. . |
| 5,439,001 | 8/1995 | Butterfield . |
| 5,494,043 | 2/1996 | O'Sullivan et al. . |
| 5,617,867 * | 4/1997 | Butterfield et al. .................. 600/503 |
| 5,634,467 | 6/1997 | Nevo . |
| 5,642,733 * | 7/1997 | Archibald et al. ................... 600/485 |
| 5,649,542 | 7/1997 | Archibald et al. . |
| 5,832,924 * | 11/1998 | Archibald et al. ................... 600/500 |
| 5,848,970 | 12/1998 | Voss et al. . |
| 5,876,346 * | 3/1999 | Corso ................................... 600/503 |
| 5,908,027 * | 6/1999 | Butterfield et al. ................. 600/503 |
| 5,964,711 | 10/1999 | Voss et al. . |

FOREIGN PATENT DOCUMENTS

| | | | |
|---|---|---|---|
| 284095 | 9/1988 | (EP) | ............................. A61B/5/02 |
| 818176 | 1/1998 | (EP) . | |
| WO 95/13014 | 5/1995 | (WO) | ........................... A61B/5/021 |
| WO982551 | 6/1998 | (WO) . | |

* cited by examiner

Primary Examiner—Robert L. Nasser
(74) Attorney, Agent, or Firm—Gazdzinski & Associates

(57) ABSTRACT

Apparatus is disclosed for non-invasively monitoring a subject's blood pressure, in which a pressure sensor assembly that includes a pressure transducer is compressed against tissue overlying an artery, with sufficient force to compress the artery. A motor first servo control system optimizes the amount of artery compression, which occurs at a mean transmural pressure of about zero, by modulating one side of a lever arm compressing the assembly against the tissue, creating a pressure signal indicative of transmural pressure. Since different pressure effects are realized according to the amount of artery compression, an appropriate control signal can be produced that provides for a second motor to adjust the other side of the lever arm to provide the optimum compression of the assembly into the tissue overlying the artery. The apparatus is optimally positioned over an artery by including an ultrasonic blood flow sensor configured to sense the flow of blood under the pressure transducer.

14 Claims, 8 Drawing Sheets

APPARATUS AND METHOD FOR NON-INVASIVELY MONITORING A SUBJECT'S ARTERIAL BLOOD PRESSURE

This application is related to U.S. patent application Ser. No. 08/766,810, now U.S. Pat. No. 5,848,970, and a divisional application thereof, application Ser. No. 09/054,288, now U.S. Pat. No. 5,964,711. This application is also related to U.S. patent application Ser. No. 09/120,069.

BACKGROUND OF THE INVENTION

This invention relates generally to apparatus and methods for monitoring a subject's arterial blood pressure and, more particularly, to such apparatus and methods that monitor arterial blood pressure non-invasively by applying a pressure sensor against tissue overlying an arterial blood vessel, to partially applanate or compress the vessel.

Two well-known techniques have been used to non-invasively monitor a subject's arterial blood pressure waveform, namely, auscultation and oscillometry. Both techniques use a standard inflatable arm cuff that occludes the subject's brachial artery. The auscultatory technique determines the subject's systolic and diastolic pressures by monitoring certain Korotkoff sounds that occur as the cuff is slowly deflated. The oscillometric technique, on the other hand, determines these pressures, as well as the subject's mean pressure, by measuring actual pressure changes that occur in the cuff as the cuff is deflated. Both techniques determine pressure values only intermittently, because of the need to alternately inflate and deflate the cuff, and they cannot replicate the subject's actual blood pressure waveform. Thus, true continuous, beat-to-beat blood pressure monitoring cannot be achieved using these techniques.

Occlusive cuff instruments of the kind described briefly above generally have been effective in sensing long-term trends in a subject's blood pressure. However, such instruments generally have been ineffective in sensing short-term blood pressure variations, which are of critical importance in many medical applications, including surgery.

One technique that has been used to provide information about short-term blood pressure variations is called arterial tonometry. One device for implementing this technique includes a rigid array of miniature pressure transducers that is applied against the tissue overlying a peripheral artery, e.g., the radial artery. The transducers each directly sense the mechanical forces in the underlying subject tissue, and each is sized to cover only a fraction of the underlying artery. The array is urged against the tissue, to applanate the underlying artery and thereby cause beat-to-beat pressure variations within the artery to be coupled through the tissue to the transducers.

The rigid arterial tonometer described briefly above is subject to several drawbacks. First, its discrete transducers are relatively expensive and, because they are exposed, they are easily damaged. In addition, the array of discrete transducers generally is not anatomically compatible with the continuous contours of the subject's tissue overlying the artery being sensed. This has led to inaccuracies in the resulting transducer signals. In addition, in some cases, this incompatibility can cause tissue injury and patient discomfort. Another drawback is that such rigid arterial tonometers have failed to correct for signal artifacts that arise when the subject's arm is moved. This is a particular problem when the subject is exercising or otherwise ambulating.

Yet another drawback to the arterial tonometer described briefly above is its inability to continuously monitor and adjust the level of arterial wall compression to an optimum level of zero transmural pressure. Generally, optimization of arterial wall compression has been achieved only by periodic recalibration. This has required an interruption of the patient monitoring function, which sometimes can occur during critical periods. This drawback is perhaps the most severe factor limiting acceptance of tonometers in the clinical environment.

Another device functioning similarly to the arterial tonometer includes a housing having a closed, liquid-filled chamber with one wall of the chamber defined by a flexible diaphragm. The device is applied against a subject's skin, with the flexible diaphragm pressed against the tissue overlying a peripheral artery, e.g., the radial artery, and several electrodes located in separate compartments of the chamber sense volume changes in the compartments that result from the beat-to-beat pressure variations in the underlying artery. Although the device seeks to replicate the arterial pressure waveform, it is considered to have a relatively low gain, making it unduly susceptible to noise. Further, the device must be calibrated periodically, during which time its continuous monitoring of the subject's blood pressure waveform necessarily is interrupted.

It should, therefore, be appreciated that there is a continuing need for an apparatus, and related method, for non-invasively and continuously monitoring a subject's blood pressure, with reduced susceptibility to noise and without the need to intermittently interrupt the device's normal operation for calibration. Various embodiments of the present invention can fulfill some or all of these requirements.

SUMMARY OF THE INVENTION

The present invention resides in an improved apparatus, and related method, for non-invasively monitoring a subject's arterial blood pressure, with reduced susceptibility to noise and without the need to intermittently interrupt the pressure monitoring for calibration. The apparatus includes a pressure transducer that produces a pressure signal indicative of the pressure applied against it and further includes a coupling device that urges the pressure transducer into compressive association and engagement with tissue overlying the subject's blood vessel, to compress the vessel and ensure that pressure variations within the vessel are coupled through the tissue to the pressure transducer.

A controller controls the coupling device to controllably modulate the location of the pressure transducer relative to a nominal location that is static with respect to the subject's blood vessel. The controller also monitors the resulting effect of the modulation on the pressure signal, producing an error signal (i.e., a control signal) that is indicative of the deviation of the nominal location from a preferred target location. Preferably, the coupling device is configured to respond to the error signal by controllably adjusting the nominal location toward the target location. When the nominal location is at or substantially close to the target location, the blood vessel is compressed according to a prescribed requirement, which is preferably a prescribed mean amount providing a transmural pressure of substantially zero. This requirement optimizes the coupling between the blood vessel and the sensor assembly. The pressure sensor assembly thereby senses the subject's blood pressure in an optimal manner.

More particularly, in one form of the invention, the pressure sensor assembly includes a base configured to provide reaction forces for urging the pressure transducer into compressive association with the tissue overlying the subject's blood vessel. The coupling device includes a first variable positioning device, such as a first motor with an eccentric cam, configured to controllably adjust the nominal location toward the target location. The coupling device also includes a second variable positioning device, such as a second motor with an eccentric cam, configured to vary the pressure transducer through a range of locations relative to the nominal location, i.e., modulating the pressure transducer about the nominal location.

Preferably, the first and second variable positioning devices actuate a first and second end of a lever arm, respectively, to actuate the pressure transducer, which is connected to the lever arm between the two ends. By monitoring the effect on the pressure signal of the second variable positioning device, the controller can direct the first variable positioning device to adjust the lever arm such that the nominal location moves, and thus the subject's blood vessel becomes compressed by the prescribed mean amount.

In a separate aspect of the invention, the pressure transducer is in compressive association with the tissue and blood vessel through a substantially incompressible, and preferably compliant plug, whereby the pressure signal is a reasonably accurate representation of the pressure being applied to the plug by the tissue. The plug preferably fills a chamber that connects the pressure transducer to the tissue. For the purposes of this application, a plug is broadly defined to be any intermediary device that puts the pressure transducer in compressive association with the tissue. For example, the plug might comprise a liquid sealed into a chamber by a flexible diaphragm, where the diaphragm contacts the tissue and the liquid contacts the pressure transducer. Likewise, the plug might be a rigid, solid device in contact with both the pressure transducer and the tissue.

In another separate aspect of the invention, the pressure transducer is configured to be in compressive association with a first portion of the tissue overlying the subject's blood vessel. A compression surface of the device is configured to compress a second portion of the tissue overlying the subject' blood vessel, the second portion preferably being a section of tissue surrounding the first portion of the tissue. The compression surface preferably compresses the second portion of tissue in concert with the pressure transducer's compressing of the first portion of tissue. This will preferably cause the pressure transducer to only sense the pressure immediately beneath it, minimizing edge effects and the pounding of artery pressure against the edge of the occluded section of the vessel.

It is also preferable that the compression surface includes an inner section and an outer section, the outer section being more compliant that the inner section. This may, in some embodiments, further minimize edge effects and pounding, as well as potentially adding to the subject's comfort due to the compliant portion forming a radius to transition between the compressed and non-compressed portions of the arm.

Another aspect of the invention resides in a blood vessel sensor carried on a housing that contains the pressure transducer. The blood vessel sensor is configured to detect the presence, and preferably the location, of a blood vessel such as an artery, thus allowing the pressure transducer to be placed in a prescribed position overlying the subject's blood vessel. The blood vessel is preferably a blood flow sensor that senses the flow (although, not necessarily the flux) of blood in the space adjacent to the housing. The blood flow sensor is preferably an ultrasonic transducer having a substantially planar face that is oriented at a prescribed acute angle relative to a planar face of the housing that adjoins the tissue overlying the blood vessel (e.g., the compression surface). The ultrasonic transducer preferably senses the velocity of the blood flow, providing an indication of blood flow when the velocity is sensed. Preferably there is a coupling medium disposed on the planar face, which in various embodiments can enhance the coupling between the ultrasonic transducer and the subject's blood vessel, and can aid in the positioning of the pressure transducer.

In another embodiment, the invention may feature a controller configured to controllably modulate the position of a pressure sensor assembly relative to a nominal location (and the subject's blood vessel) with a periodic signal having a frequency substantially greater than the frequency of the subject's expected heartbeat, and the controller monitors the resulting pressure signal to produce a plurality of pressure waveforms. Each such pressure waveform corresponds to a different phase of the periodic signal, which in turn corresponds to a different nominal amount of vessel compression.

The controller is configured to select the particular one of the pressure waveforms that derives from a selected transmural pressure, preferably being a transmural pressure of substantially zero. For example, the waveform may be selected by choosing the particular waveform for which the pressure signal at systole differs from the pressure signal at diastole by a maximum amount. The controller then directs the coupling device to adjust the nominal location such that the selected waveform generally exhibits a lower mean pressure than half of the waveforms and exhibits a higher mean pressure than the other half of the waveforms.

Other features and advantages of the present invention should become apparent from the following description of the preferred embodiments, taken in conjunction with the accompanying drawings, which illustrate, by way of example, the principles of the invention.

DESCRIPTION OF THE PREFERRED EMBODIMENTS

Preferred embodiments of the present invention include variations of the apparatus and methods described below. The embodiments incorporate aspects of the invention described in U.S. patent application entitled "Apparatus and Method for Non-invasively Monitoring a Subject's Arterial Blood Pressure," Ser. No. 766,810, filed Dec. 13, 1996, ("the '810 application"), which is incorporated herein by reference.

Figure 1:
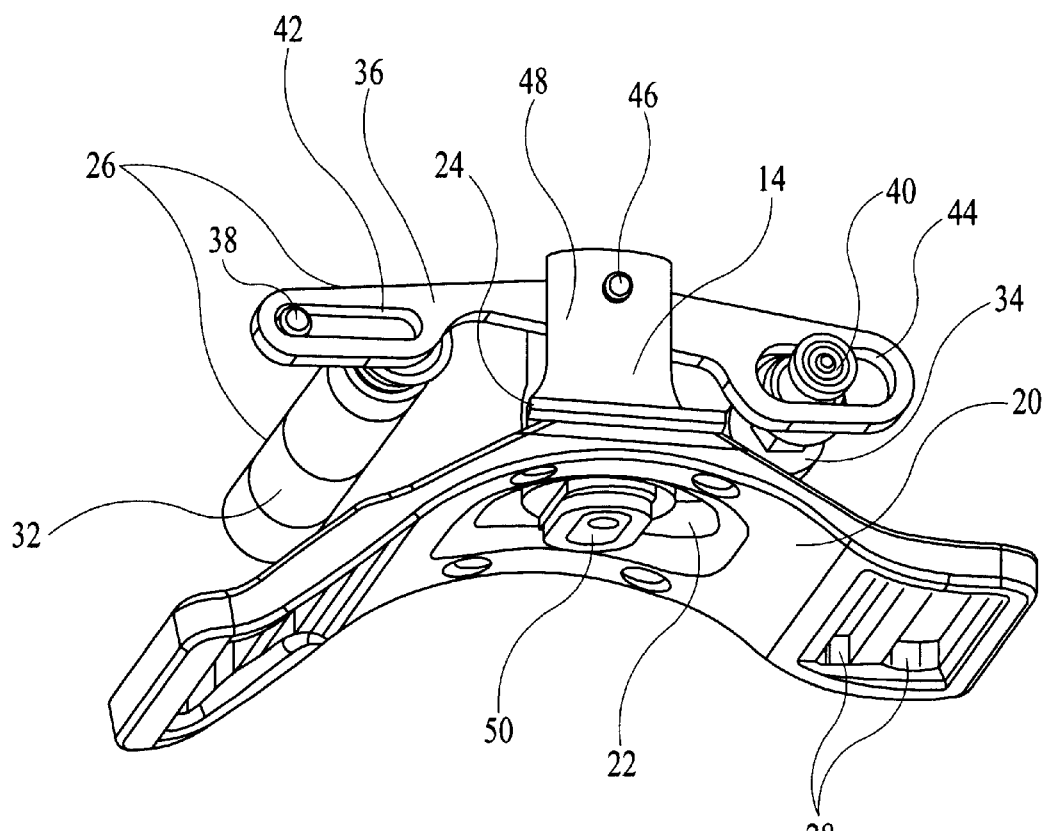
FIG. 1 is a partial, perspective view of a blood pressure monitoring apparatus embodying features of the present invention. Depicted are a base plate, a coupling device and a pressure sensor assembly of the blood pressure monitoring apparatus.
Figure 2:
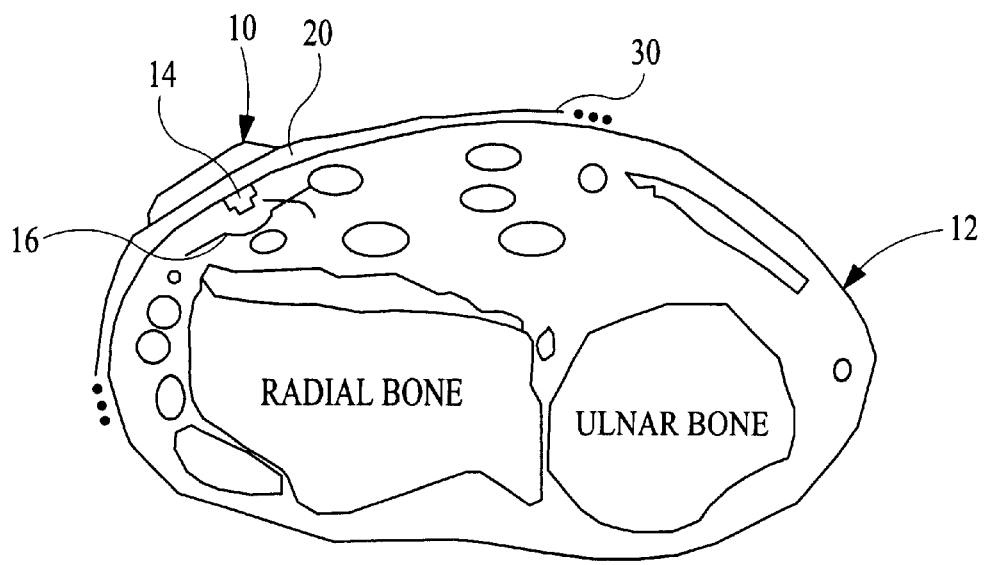
FIG. 2 is a schematic cross-sectional view of the blood pressure monitoring apparatus of FIG. 1, in its prescribed position secured to a subject's wrist, with the pressure sensor assembly disposed adjacently to the tissue overlying the subject's radial artery.

With reference now to the drawings, and particularly to FIGS. 1 and 2, there is shown a blood pressure monitoring apparatus 10 configured for attachment to a subject's wrist 12, with a pressure sensor assembly 14 compressively engaging the tissue 16 overlying the subject's radial artery 18. Blood pressure variations within the artery are coupled through the tissue to the pressure sensor assembly, to produce a pressure signal output that represents the artery's pressure waveform. The pressure sensor assembly, by engaging the tissue over the radial artery, compresses the radial artery, generally causing a partial or total occlusion of the vessel. The amount of compression affects the degree of coupling between the pressure variations within the artery and the pressure applied to the pressure sensor assembly.

Figure 3:
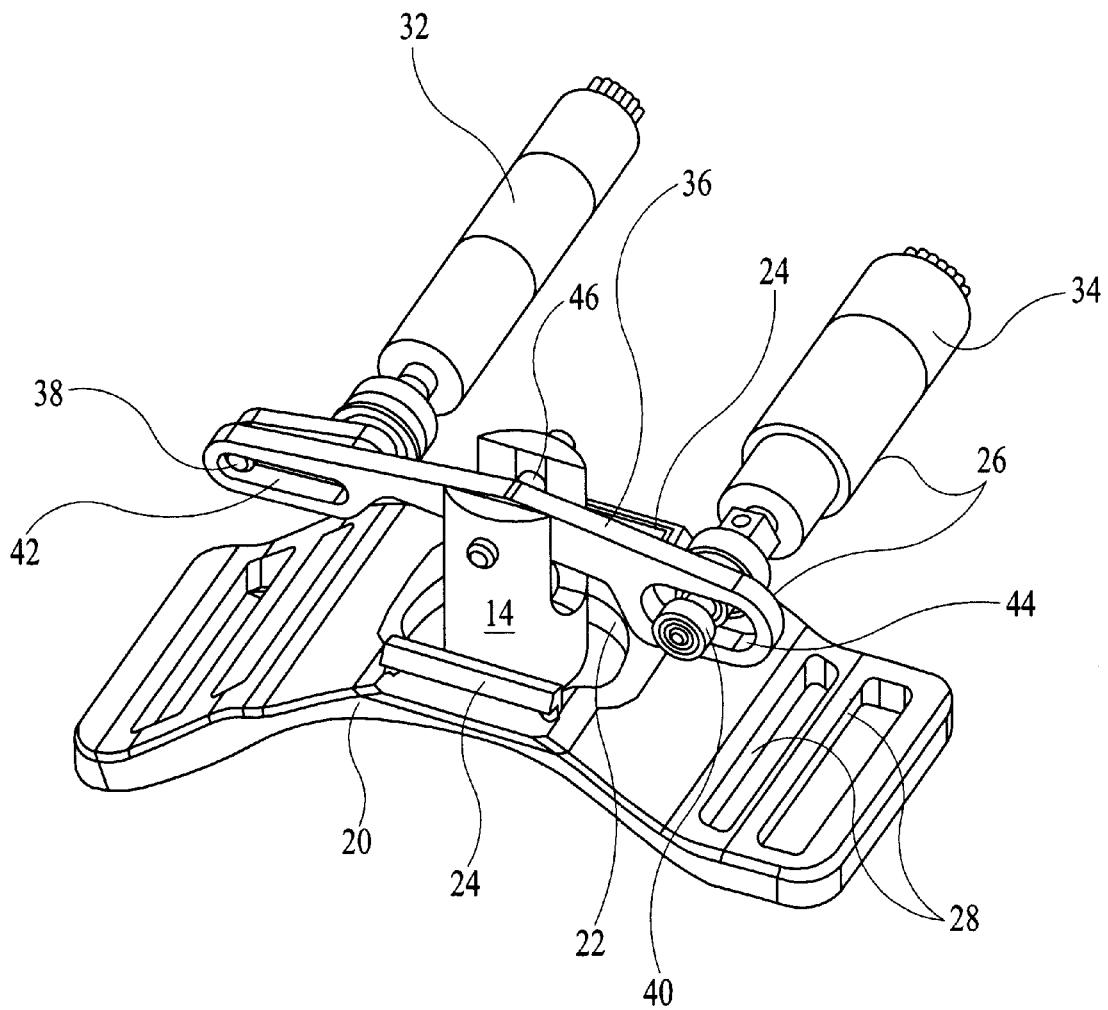
FIG. 3 is a view of the base plate, coupling device and pressure sensor assembly of FIG. 1, from a different perspective than that of FIG. 1.

As seen in FIGS. 1–3, the blood pressure monitoring apparatus 10 includes a plastic plate-like base 20 having a curved shape to conform to the subjects wrist 12. The base defines an orifice 22 configured such that the pressure sensor assembly 14 can advance through the orifice to contact the tissue 16 overlying the subject's radial artery 18. A snap-fit type/quick-release attachment 24 is formed on the base, allowing the base to quickly and easily receive a coupling device 26 configured to control the advancement of the pressure sensor assembly through the orifice, and thus to control the location of the pressure sensor assembly.

The base 20 also includes attachment loops 28 configured to receive a wrist strap 30 to hold the base in a prescribed position on the subject's wrist 12. When the blood pressure monitoring apparatus 10 is properly secured to the subject's wrist, it holds and maintains the pressure sensor assembly 14 in a location appropriate to advance into contact with the tissue 16 overlying the subject's radial artery 18.

The coupling device 26 includes a first electric motor 32, a second electric motor 34, and a lever arm 36. The two motors are affixed to a coupling device attachment (not shown) conforming to the snap-fit attachment 24 on the base 20. Thus, when the coupling device attachment is received in the base's attachment, the two motors are held in a substantially fixed position with respect to the base. Preferably, the motors' axes are at right angles to the surface of the tissue 16 overlying the subjects radial artery 18, and most preferably the motors' axes are approximately parallel to the artery.

The lever arm 36 is suspended between a first, eccentrically located cam 38 on the first motor 32, and a second, eccentrically located cam 40 on the second motor 34. Each cam 38, 40 is received within a respective slot 42, 44 on opposing ends of the lever arm, allowing the motors to drive the cams and thereby exercise control over the lever arm's orientation and location. The pressure sensor assembly 14 is connected to a central portion of the lever arm, between the two slots, by a pin 46. The motors and lever arm are thus configured such that either motor may affect the location of the pressure sensor assembly.

Figure 4:
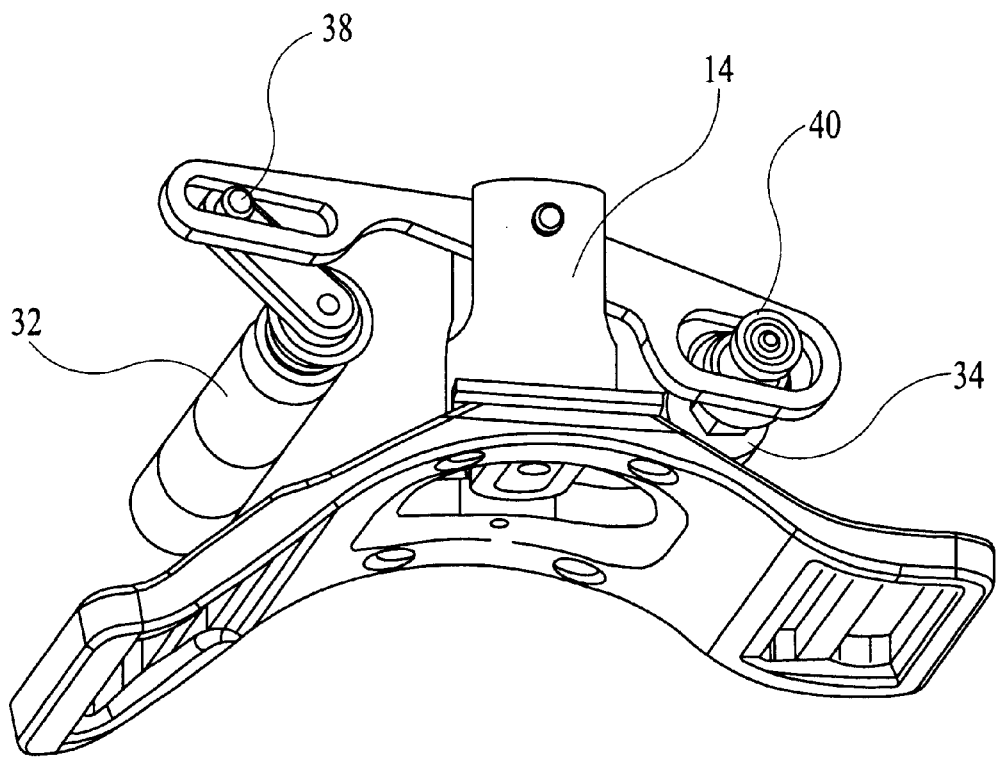
FIG. 4 is a perspective view of the base plate, coupling device and pressure sensor assembly of FIG. 1, wherein the coupling apparatus has retracted the pressure sensor assembly.
Figure 5:
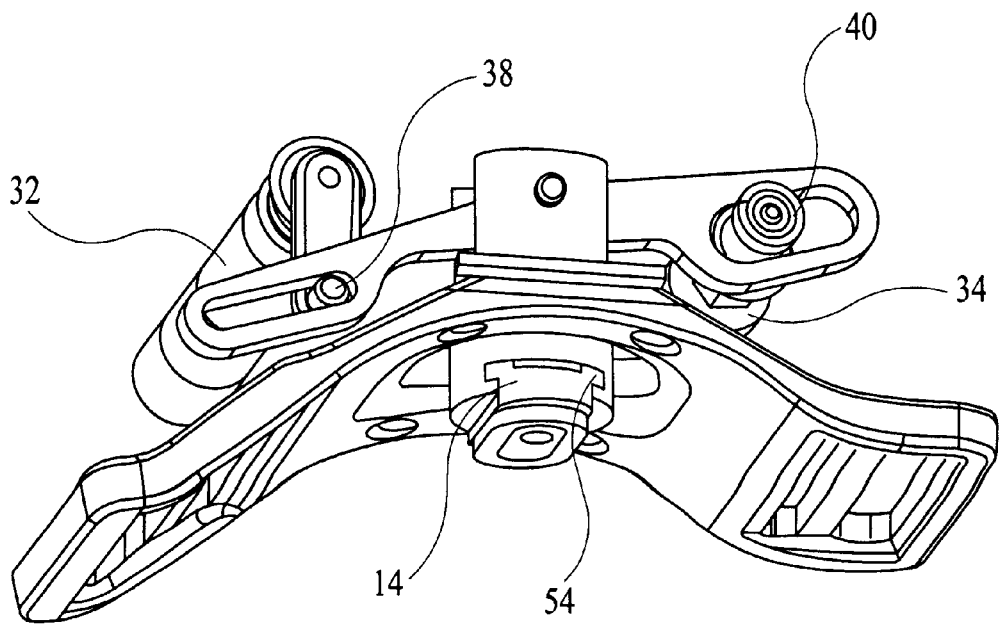
FIG. 5 is a perspective view of the base plate, coupling device and pressure sensor assembly of FIG. 1, wherein the coupling apparatus has advanced the pressure sensor assembly.

The first cam 38 is attached to the first motor 32 with a relatively large amount of eccentricity, relative to the second cam and motor, thus providing for relatively large controlled movements of the pressure sensor assembly 14. This can be seen in FIGS. 4 and 5, showing the pressure sensor assembly 14 retracted and advanced, respectively, by the first motor 32 and the first cam 38. The second cam 40 is attached to the second motor 34 with a relatively small amount of eccentricity, providing for comparatively smaller controlled movements of the pressure sensor assembly, which are not depicted.

While the motors 32, 34, their respective eccentric cams 38, 40, and the lever arm 36 provide for a preferred form of coupling device 26, a wide variety of variable positioning devices, or combinations of variable positioning devices, would be suitable for use with the invention.

Figure 6:
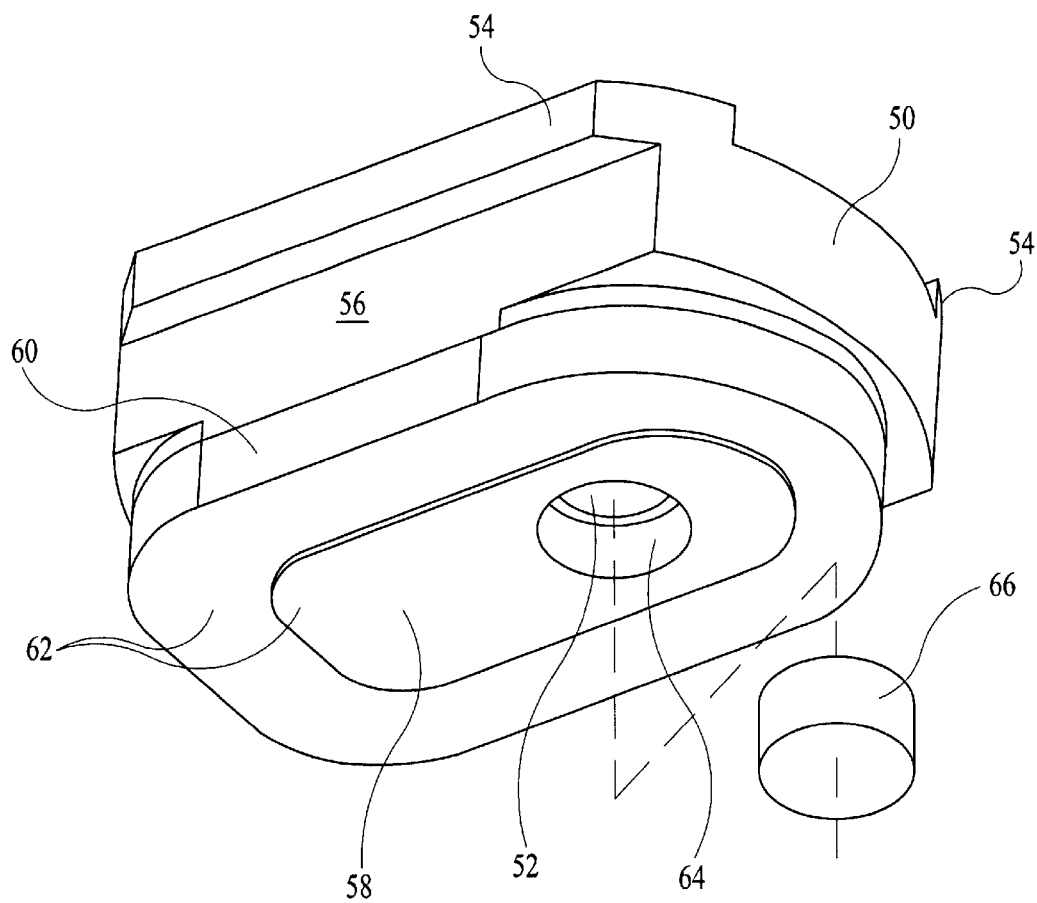
FIG. 6 is an exploded perspective view of a sensor housing that is part of the pressure sensor assembly of FIG. 1.
Figure 7:
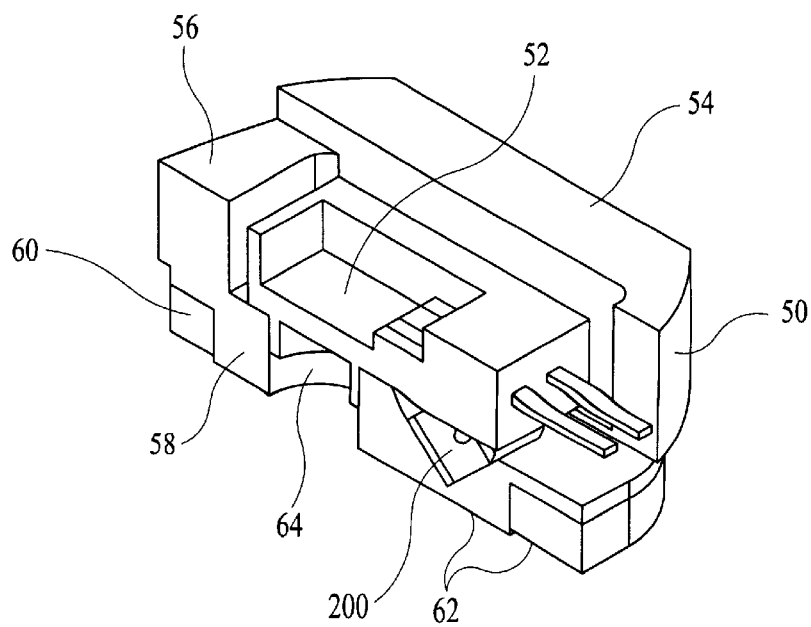
FIG. 7 is a cross-sectional view of the sensor housing of FIG. 6.

With reference to FIGS. 1, 6 and 7, the pressure sensor assembly 14 includes a sensor frame 48, a sensor housing 50, and a pressure transducer 52. The sensor frame is hingedly attached to the lever arm 36 by the pin 46, and thus can pistonically convert translational and rotational movement of the lever arm, caused by the cams, into a translational motion. The sensor housing includes two flanges 54 (see FIG. 5) that conform to two slots in the sensor frame, providing for the sensor housing to be slidingly removable from the sensor frame for ease of service and replacement. The pressure transducer is carried by the sensor housing, and is configured to convert pressure applied against it to an electrical signal indicative of the pressure level.

The sensor housing includes a substantially rigid, preferably plastic portion 56 that includes the flanges 54, and also includes a protrusion 58 having a roughly oval/elliptical cross-section (i.e., having a cross-sectional length greater than a cross-sectional width, and having rounded corners). The cross-sectional length is preferably configured to extend along the blood vessel, thus providing compression along a length of vessel while minimizing the compression of surrounding tissue, and minimizing interference from bones and tendons. Alternatively, the rigid portion may be metal or some other relatively rigid material. It may be preferable that the rigid portion is more compliant than bone, and is less compliant than interstitial tissue and arterial wall.

The protrusion is surrounded by a conforming ring 60 composed of a relatively compliant material such as room temperature vulcanizing rubber (RTV) or silicone. The protrusion and the ring include surfaces combining to form a flat compression surface 62 that is relatively rigid in an inner section (the protrusion) and relatively compliant in an outer section (the ring).

The compression surface 62 is interrupted by an opening to a chamber 64, formed in the protrusion 58. The chamber extends from the compression surface up to the pressure transducer 52. The chamber is preferably filled with a plug 66, in the form of an incompressible, and preferably compliant material, such as RTV. The plug forms a surface, across the chamber opening, that is flush with the compression surface. Filling the chamber entirely, the plug also presses up against the pressure transducer. Thus, when the sensor housing 50 is pressed against the tissue 16 overlying the subjects radial artery 18, the pressure transducer is in compressive association, through the plug and the skin directly underlying the plug, with a first portion of the tissue overlying the subject's radial artery, and thus with the radial artery itself.

At the same time, the compression surface 62 compresses a second portion of the tissue overlying the subject's radial artery 18, the second portion of the tissue surrounding the first portion of the tissue. The sensor housing, the pressure transducer and the plug all move in conjunction with each other, providing for the first and second portions of the tissue to be compressed in a flush, uniform fashion. This provides for the portion of the artery that is compressed and occluded to extend beyond the more limited portion that is in compressive association with the pressure transducer 52, and thus shields the pressure transducer from spurious pressure information caused by the blood in the artery having to pass into the portion of the artery that is compressed and occluded. It also diminishes the flow to the artery underlying the pressure sensor during periods of positive transmural pressure.

As is described in the '810 application, if the artery 18 is compressed by an amount that corresponds to a mean transmural pressure near zero, the pressure variation of a normal heartbeat, about 50 mmHg (i.e., 50 millimeters of mercury) will cause a relatively large change in the artery's effective diameter, as compared to the artery's change in diameter at non-zero mean transmural pressures. This provides for a maximum coupling between the arterial pressure and the pressure transducer's output signal. It is desirable, therefore, to regulate the mean arterial compression to match this optimum value.

To this end, the coupling device 26 controls the location of the pressure sensor assembly 14. In particular, the coupling device implements a control scheme that locates the pressure sensor assembly so as to compress the tissue 16 overlying the subject's radial artery 18 to provide optimal compression of the radial artery. While a preferred control scheme is to maintain the mean transmural pressure at zero, a variety of other requirements (e.g., holding either the mean pressure or the maximum and minimum pressures within prescribed bounds) might alternatively be prescribed to produce optimal or preferable results.

Under the preferred control scheme, the coupling device 26 actively varies, or modulates, the location of the entire pressure sensor assembly 14, including the pressure transducer 52, toward and away from the blood vessel, relative to a nominal location. For example, the coupling device could sinusoidally cycle the pressure sensor assembly relative to a nominal location that is the mean position of the cycle. The modulating location of the pressure sensor assembly modulates, or dithers, the compression of, and thereby the effective diameter of, the subject's radial artery 18 underlying the pressure sensor assembly. The effect of the modulating artery diameter on the pressure signal is then analyzed, providing information on the transmural pressure, as is described in the '810 application.

The coupling device 26 effects this modulation of the artery's diameter by imparting a 25-Hz sinusoidal motion to the pressure sensor assembly 14. This sinusoidal motion is produced by the second motor rotating at 25-Hz, causing the second cam to move one end of the lever arm at that rate. A 25-Hz frequency is selected, because it is generally higher than the highest frequency components of interest in the artery's blood pressure waveform, and thus the pressure signal may be accurately filtered for its modulation and heartbeat components.

If the artery 18 is under-compressed, then the ac pressure response to the 25-Hz oscillation will be larger during systole than during diastole. Conversely, if the artery is over compressed, then the ac amplitude of the 25-Hz pressure oscillation will be larger during diastole than during systole. However, if the artery 21 is optimally compressed, then the ac amplitudes of the 25-Hz pressure oscillation during the systolic and end-diastolic stages will be substantially the same. In addition, the overall amplitude of the pressure oscillation is at a minimum when the artery is optimally compressed. With this information, regarding the under-or over-compression of the artery, the movement of the pressure sensor assembly 14 may be adjusted such that the nominal location moves toward a target location at which the artery is compressed to the optimum mean amount.

A control system for implementing the control scheme described above is depicted in FIG. 8. An oscillator 100 controls the speed of the second motor 34 to cyclically compress the artery 18 at 25-Hz. In addition to the coupling device 26 and the pressure sensor assembly 14, identified above, the control system further includes a 25-Hz bandpass filter 102 that filters the pressure signal received on line 104 from the pressure transducer 52.

The filtered signal, which incorporates only the 25-Hz component of the pressure signal, is supplied on line 106 to an analyzer 108. The analyzer receives the filtered signal and compares its ac amplitude during systole with its ac amplitude during diastole, to determine whether the artery is under compressed, over compressed, or optimally compressed. The analyzer then produces a corresponding error signal that is supplied on line 110 to the first motor 32, which adjusts the lever arm 36 to appropriately adjust the nominal location toward the target location.

Operation of the controller system automatically regulates the position of the pressure sensor assembly 14 such that the assembly optimally compresses the subject's radial artery 18. For example, if the analyzer 108 determines that the ac amplitude of the filtered pressure signal is greater during systole than it is during diastole, then a positive error signal is produced, and the first motor 32 is adjusted to advance the nominal location of the pressure sensor assembly and thereby increase the compression of the artery. The opposite would occur if the controller determines that the filtered pressure signal's ac amplitude is greater during diastole than it is during systole.

To provide a visible display of the subject's arterial pressure waveform, the blood pressure monitoring apparatus 10 furter includes a 25-Hz band stop filter 112 and a display 114. The filter receives the pressure signal on line 104 from the pressure transducer 52, and it samples this signal at a rate of 50 samples per second. This sampling is phased with the 25-Hz modulation signal output on line 116 by the oscillator 100 such that it always occurs at the modulation signal's zero crossings. The sampled pressure signal then is coupled on line 118 to the display 120, for real-time display. The sampled pressure signal is also coupled on line 118 to the analyzer 108, to be used for determining the timing of systole and diastole.

Figure 8:
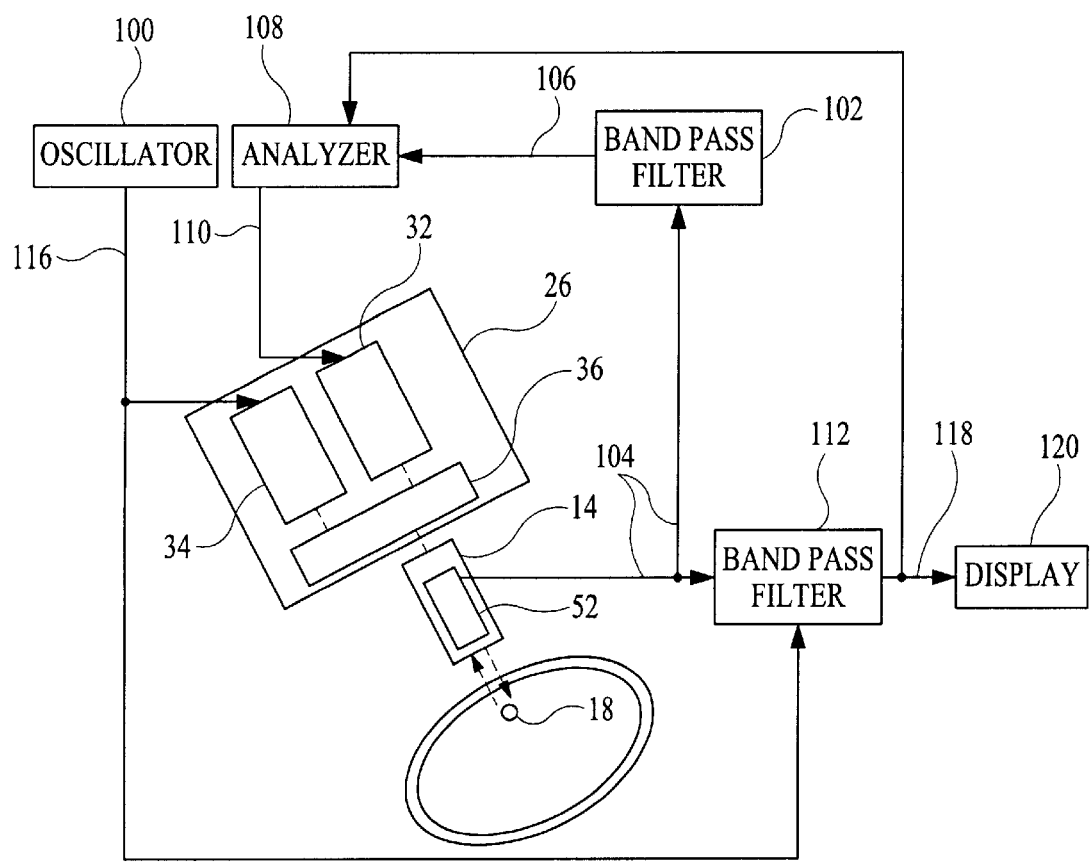
FIG. 8 is a block diagram of a first embodiment of a blood pressure monitoring apparatus in accordance with the invention, incorporating the coupling device and pressure sensor assembly of FIG. 1.
Figure 9:
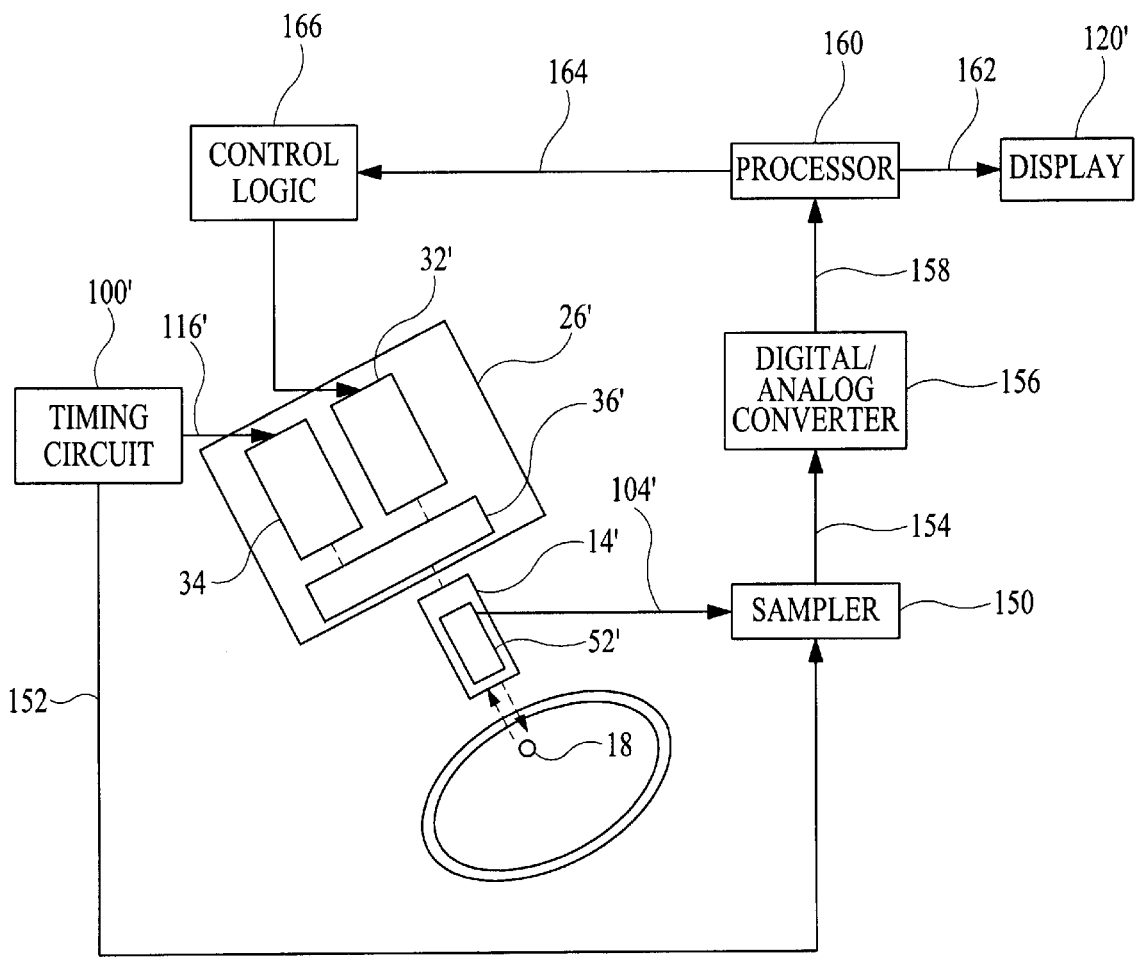
FIG. 9 is a block diagram of a second embodiment of a blood pressure monitoring apparatus in accordance with the invention, which incorporates the coupling device and pressure sensor assembly of FIG. 1 and provides an accurate depiction of a subject's arterial pressure waveform within as little as a single heartbeat.

In an independent feature of the invention, an accurate depiction of the subject's blood pressure waveform, and an accurate measurement of arterial pulse pressure amplitude, can be produced within as little as a single heartbeat using a monitoring apparatus embodying the invention under a control system, as depicted in FIG. 9, which implements a special control and monitoring algorithm. Some elements of the apparatus of FIG. 9 correspond to elements of the apparatus of FIG. 8, and these elements are identified by the same reference numerals, but with an added prime (') symbol.

More particularly, and with reference to FIG. 9, coupling device 26', including a first motor 32', a second motor 34', and a lever arm 36', are configured to advance a pressure sensor assembly 14' against the tissue overlying the radial artery 18. The pressure sensor assembly includes a pressure transducer 52' that is configured to be held in compressive engagement with the tissue by a wrist strap. Actually, because the pressure waveform ordinarily can be produced within merely a few seconds using this feature, the wrist strap can be eliminated and the apparatus operated simply by pressing the device manually against the subject's wrist.

An oscillator, or timing circuit 100' supplies a 25-Hz sine wave signal on line 116' to the second motor 34', to cause the pressure sensor assembly 14' to be modulated, i.e., advanced into and retracted from the tissue overlying the artery 18, in a sinusoidal fashion, with respect to a nominal location. If the pressure sensor assembly is being urged against the subject's wrist such that the arterial wall is partially compressed, this modulation ordinarily will cause a corresponding sinusoidal pressure variation about a mean pressure on the pressure transducer 52'. The pressure transducer replicates this pressure variation in an analog pressure signal output on line 104'.

Figure 10A:
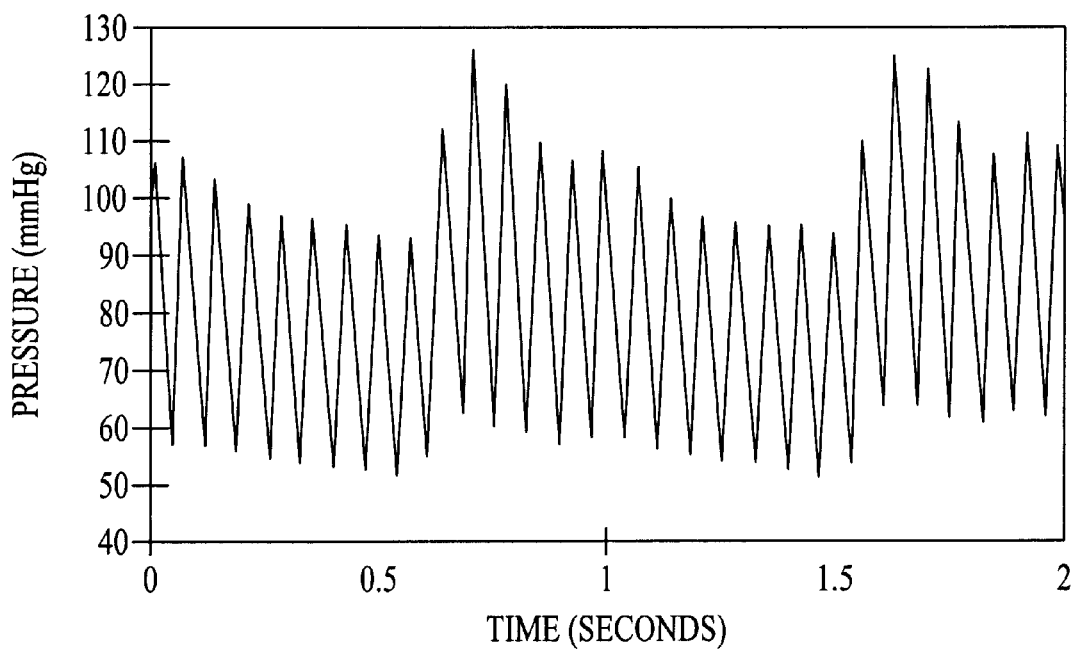
FIG. 10A is a graph of an exemplary pressure signal produced by the blood pressure monitoring apparatus of FIG. 9, incorporating both a sinusoidal modulation component and a subject heartbeat component.

One representative waveform for the analog pressure signal on line 104' is depicted in FIG. 10A, which corresponds to a situation in which the pressure sensor assembly 14' is being urged against the subject's wrist with a mean pressure of about 80 mmHg. It will be noted that the pressure signal includes not only a 25-Hz modulation component, but also a heartbeat component. The apparatus of FIG. 9 functions effectively to demodulate this waveform and thereby to produce an accurate representation of the subject's actual blood pressure waveform.

The apparatus of FIG. 9 achieves this demodulation by sampling the analog pressure signal on line 104' at a sample rate that is an integral multiple of the 25-Hz modulation frequency. At a sample rate of 1600-Hz, for example, 64 samples would be provided for each modulation cycle. Since the first sample of each successive modulation cycle is produced while the 25-Hz modulation component is at the same level, it follows that these first samples can be associated together to produce a depiction of the subject's variable arterial pressure for that particular level. The same is true for each of 64 separate sets of samples. Thus, 64 separate pressure waveforms can be generated, each representing a different nominal arterial compression.

Figure 10B:
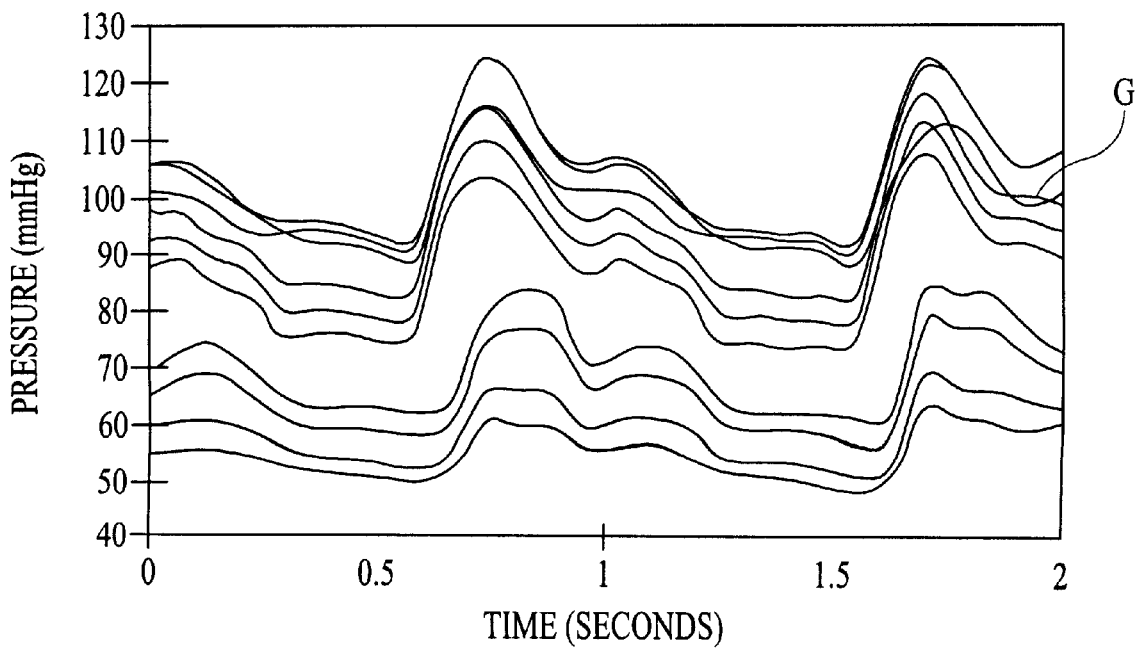
FIG. 10B is a graph of ten reconstructed pressure waveforms reconstructed from the exemplary pressure signal of FIG. 10A by the blood pressure monitoring apparatus of FIG. 9.

Ten exemplary waveforms of these 64 separate pressure waveforms are depicted in FIG. 10B. It will be noted that the waveform having the lowest magnitude represents the pressure samples that are made when the 25-Hz modulation waveform is at its lowest value, and that the waveform having the highest magnitude represents the pressure samples that are made when the 25-Hz modulation waveform is at its highest value. The particular one of the waveforms that provides the greatest difference between the systolic pressure and diastolic pressure is deemed to be the one produced when the subject's artery is compressed by the particular amount that provides optimal coupling to the pressure transducer 52'. In the exemplary case depicted in FIG. 10B, this particular waveform is depicted by the bold reference line G.

It will be appreciated that the particular one of the 64 waveforms that is considered optimal will vary depending on the nominal pressure applied by the pressure sensor assembly 14' to the subject's wrist. If the nominal pressure is relatively low, then the optimal waveform will likely be one of the higher-level waveforms, which are produced when the 25-Hz modulation signal is at or near its positive peak. On the other hand, if the nominal pressure is relatively high, then the optimal waveform will likely be one of the lower-level waveforms, which are produced when the 25-Hz modulation signal is at or near its negative peak.

With reference again to FIG. 9, the successive samples of the analog pressure signal on line 104' are produced by a sample-and-hold or sampler circuit 150, under the guidance of a 1600-Hz clock signal supplied on line 152 from the timing circuit 100'. The resulting samples are supplied on line 154 to an analog-to-digital converter 156, which produces a succession of digital words that are coupled on lines 158 to a suitable processor 160. The processor associates together the successive samples, as discussed above, acting as a comb filter to produce the 64 separate waveforms. It then ascertains the particular waveform that corresponds to the optimum level of nominal artery compression, which is preferably the waveform having the largest pulse amplitude. This particular waveform is then coupled via line 162 to a display 120'.

While the optimal waveform may be any of the 64 waveforms, it is preferable that the optimal waveform is close to or exactly the middle waveform. This provides for the artery to have a mean transmural pressure of approximately zero throughout the modulation. To close the loop, providing feedback to appropriately adjust the nominal pressure, the processor 160 analyses the relative levels of the optimal waveform with respect to the other waveforms. Preferably, the processor compares the arithmetical average (i.e., mean) pressure for each set of waveform data. If the optimal waveform is at a lower pressure than most waveforms, then the nominal pressure applied to the wrist should be reduced. Similarly, if the optimal waveform is at a higher pressure than most, then the nominal pressure applied to the wrist should be increased.

After each heart beat, the processor determines the desired change to the nominal pressure, if any, and provides this information on line 164 to a control logic circuit 166 that controls the first motor 32'. The first motor then actuates the lever arm 36' to adjust the nominal location of the oscillation toward a target location where the pressure sensor assembly 14' compresses the artery 18 to have a mean transmural pressure of approximately zero. As the optimal waveform approaches the middle of the waveforms, the amplitude of the 25-Hz modulation may be reduced to maintain the high and low transmural pressures near the mean transmural pressure at approximately zero.

The apparatus of FIG. 9 can be used with sampling rates of varying multiples of the modulation frequency, with higher rates being preferable for accuracy, and lower rates being preferable for computational simplicity. Furthermore, numerical approximation techniques can be used to practice this invention without having a sampling frequency that is a precise multiple of the modulation rate, however, such an embodiment is not preferred.

The two embodiments described above, incorporating the two distinct features of the invention, being depicted in FIGS. 8 and 9, both presume that the pressure sensor assembly 14 or 14' is correctly circumferentially positioned with respect to the arm in order to properly compress the artery 18. While skilled professionals and/or experienced subjects might become proficient at placement of the blood pressure monitoring apparatus 10, the device preferably includes a mechanism designed to guide the circumferential positioning of the pressure sensor assembly with respect to the subject's arm.

To this end, with reference to FIG. 7, the blood pressure monitoring apparatus 10 further incorporates a blood vessel sensor, preferably in the form of a blood flow sensor. The blood flow sensor could be of any functional type, such as using lamps, tones, or the like, and could sense any type of characteristic indicative of blood flow, such as blood velocity. The blood flow sensor is preferably an ultrasound system for use in controllably positioning the pressure sensor assembly 14 in its prescribed position immediately overlying the subject's radial artery 18. Other sensors capable of detecting the presence of a blood vessel (including those capable of detecting the presence of blood) are within the scope of the invention.

The ultrasound system includes an ultrasonic transducer 200 in the form of a piezoelectric device, which is carried within a recess 202 of the plastic portion 56 of the sensor housing 50, adjacent to the chamber 64 that carries the pressure transducer 52. The ultrasonic transducer is conditioned to emit a series of ultrasonic bursts into the tissue adjacent to the pressure transducer.

The bursts are scattered by red blood cells flowing through the artery, and the ultrasonic transducer receives back a portion of the scattered bursts. The scattered bursts are Doppler shifted according to the velocity of the blood. The ultrasound system then compares the frequencies and phase angles of the transmitted and returned bursts, and it monitors the magnitude of the comparison signal to determine the proximity of the ultrasonic transducer to the artery. This allows the pressure sensor assembly to be controllably moved across the subject's wrist until its prescribed position overlying the radial artery has been reached. Optionally, this may also be used to determine the blood flow velocity.

More particularly, the oval shape of the compression surface conveniently allows for the pressure transducer and the ultrasonic transducer to be conveniently placed next to each other. The sensor housing recess 202 that carries the ultrasonic transducer 200 has a shape that is generally oriented at an angle of about 35 degrees relative to the sensor housing's planar compression surface 62, facing the pressure transducer chamber 64. The ultrasonic transducer is secured within its recess, and it is conditioned to emit bursts of ultrasonic energy axially out of the recess, into the space immediately underlying the pressure transducer chamber. With the oval shape aligned with the vessel, the ultrasonic transducer may be positioned downstream (relative to the blood flow) from the pressure transducer, emitting the bursts in an upstream direction. In order to improve the connection between sensor housing and the skin, air gaps are preferably removed using some form of gel. Alternatively, a semi-cured, sticky (tacky) RTV could be used.

Because of the specified acute angle, a component of the emitted bursts inherently will be aligned with the axis of the subject's radial artery 18, such that the flow of blood through the artery can be readily detected using standard Doppler detection. An ultrasonic transducer 200 orientation angle in the range of about 30 to 60 degrees is considered suitable, although 35 degrees is preferred. Upon passing through the material interface from the sensor housing to the tissue, waves from the ultrasonic transducer bend to a preferred angle of 45 degrees.

Figure 11:
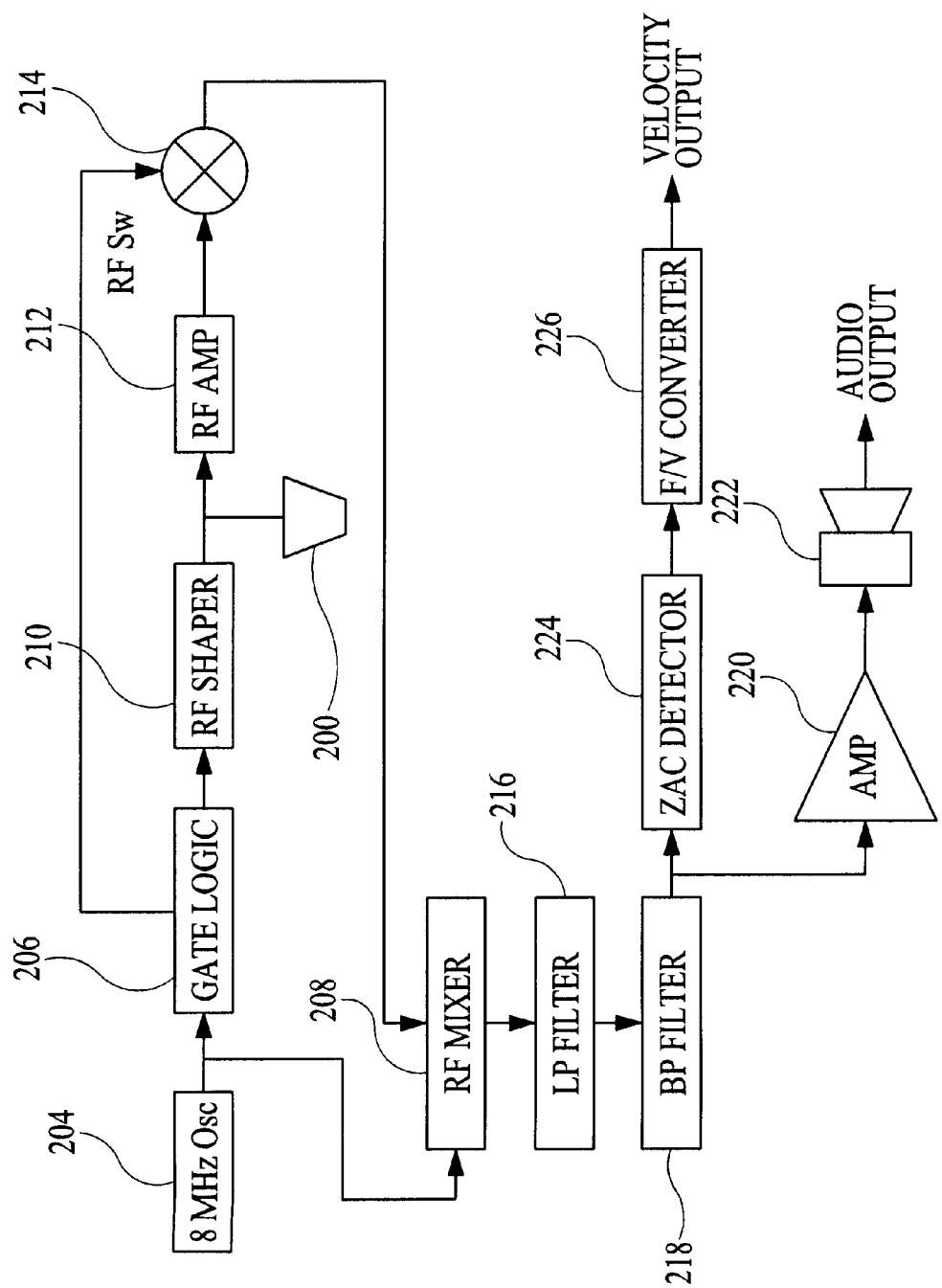
FIG. 11 is a block diagram of the signal processing portion of an ultrasound system, used to controllably position pressure sensor assembly of FIG. 1 on a subject's wrist.

FIG. 11 is a simplified block diagram of the signal processing portion of the ultrasound system, used to controllably position the pressure sensor assembly 14 in its prescribed position on the subject's wrist. An oscillator 204 generates a continuous square wave signal, having a fixed frequency of about 8 MHz, for coupling to a gate logic circuit 206 and to an rf mixer 208. The gate logic circuit transmits 8 microsecond bursts of the 8 MHz signal, interrupted by 8 microsecond dead times. An rf shaper circuit 210 converts the resulting series of square wave bursts from the gate logic circuit into corresponding sine wave bursts, for application to the ultrasonic transducer 200. The ultrasonic transducer thereby is conditioned to transmit a succession of 8 MHz bursts of sonic energy into the adjacent tissue.

In use, the transmitted bursts of sonic energy are scattered by red blood cells flowing through the subject's radial artery 18, and a portion of the scattered energy is directed back toward the ultrasonic transducer 200. The time required for the return energy to reach the ultrasonic transducer varies according to the speed of sound in the tissue and according to the depth of the artery. Typical transit times are in the range of 6 to 7 microseconds.

The ultrasonic transducer 200 is used to receive the reflected ultrasound energy during the dead times between the successive transmitted bursts. The ultrasonic transducer therefore produces a receive signal, of relatively low magnitude, and this receive signal is coupled to an rf amplifier 212, for amplification. The amplified signal is then supplied to an rf switch 214, which gates the signal to the rf mixer 208 only during the dead times between successive transmitted bursts. The rf mixer mixes these gated bursts with the original 8 MHz signal received from the oscillator 204.

The frequency of the ultrasonic transducer's transmit signal will differ from that of the return signal, because the scattering red blood cells within the radial artery 18 are moving. Thus, the return signal, effectively, is frequency modulated by the blood flow velocity. The signal output by the rf mixer 208, therefore, will incorporate the 8 MHz fundamental frequency, as well as sum and difference frequencies of the transmit and return signals. This output signal is supplied to a low-pass filter 216, for removal of the 8 MHz fundamental frequency, as well as any higher-order harmonics. A bandpass filter 218 then removes all signal components other than those components representing the actual blood velocity.

The signal output by the bandpass filter 218 is supplied to an audio amplifier 220, and in turn to a speaker 222, to enable an operator to hear a representation of the blood velocity signal and thereby to determine when the pressure sensor assembly 14 is located approximately over the radial artery 18. The output signal also is supplied to a zero-axis crossing detector 224, which functions like a one-shot circuit to produce a pulse each time the signal crosses a zero axis. These pulses are supplied to a frequency-to-voltage converter circuit 226, which produces a dc output signal indicative of frequency and thus of the blood flow rate. This signal can be displayed and/or recorded for further analysis.

In an alternative embodiment (not shown in the drawings), the ultrasound system includes an array containing a plurality of ultrasonic transducers, preferably being three or more transducers, arranged along an axis perpendicular to the direction toward the pressure transducer 52. By comparing the relative strengths of the signals derived from the ultrasonic transducers, a determination of the correct direction for moving the pressure sensor assembly 14 to its prescribed position overlying the subject's radial artery 18 can be readily ascertained. A lateral adjustment mechanism, such as a turn screw, may be manually driven in response to the error signal, or may be automatically controlled by a controller in response to the error signal.

In another alternative embodiment (likewise not shown in the drawings), a single ultrasonic transducer is configured to be controllably tiltable, so as to sweep its ultrasound bursts across the subject's wrist. The particular tilt direction that yields a Doppler signal of maximum strength indicates how the pressure sensor assembly 14 must be moved to reach its prescribed position overlying the subject's radial artery 18. This system preferably provides directional information for the position of the blood vessel. Alternatively, the transducer tilting mechanism can be replaced by a reflector with a tilting or turning mechanism that oscillates to steer the signals.

Various embodiments of the invention may provide for displays that include information on the systole, the mean, the diastole, the heart rate, the time-tension index and the pressure waveform. The information may be graphically and/or numerically presented. Furthermore, the information may be passed to data storage machines or other devices requiring the information.

It should be appreciated from the foregoing description that the present invention provides an improved apparatus for monitoring a subject's blood pressure, non-invasively, in which a pressure sensor assembly, incorporating a pressure transducer, is compressed against tissue overlying an artery with sufficient force to compress the artery by an amount that optimally couples pressure waveforms within the artery. In addition, while the position of the pressure sensor assembly is modulating, the nominal location of the pressure sensor assembly is controlled to compensate for pressure variations due to arterial pulses. This minimizes variations in the artery's effective diameter, whereby the pressure applied to the pressure transducer is made to closely follow the actual arterial pulse waveform.

Although the invention has been described in detail with reference only to the preferred embodiments, those skilled in the art will appreciate that various modifications can be made without departing from the invention. Accordingly, the invention is defined only by the following claims.

We claim:

1. Apparatus for non-invasively monitoring the pressure within a subject's blood vessel, comprising:
   a housing having a substantially planar face configured to compressively engage the tissue overlying the subject's blood vessel, a chamber, and a recess;
   a pressure transducer carried on the housing and configured to produce a pressure signal indicative of the pressure applied against it, the pressure transducer further being sized to be received within the chamber of the housing;
   a coupling device configured to urge the housing into compressive engagement with the tissue overlying a subject's blood vessel, to compress the vessel and ensure that pressure variations within the vessel are coupled through the tissue to the pressure transducer; and
   a blood vessel sensor sized to be received within the recess of the housing and configured to detect the presence of the blood vessel in the space adjacent to the housing, whereby the apparatus can be moved to place the pressure transducer is in a prescribed position overlying the subject's blood vessel.

2. Apparatus as defined in claim 1, wherein:
   the pressure transducer has a substantially planar face that is oriented substantially parallel with the planar face of the housing; and
   the blood vessel sensor is an ultrasonic transducer having a substantially planar face that is oriented at a prescribed acute angle relative to the planar face of the housing.

3. Apparatus as defined in claim 2, wherein the substantially planar face of the ultrasonic transducer is oriented at an angle of about 35 degrees relative to the planar face of the housing.

4. Apparatus as defined in claim 2, wherein:
   the recess of the housing is configured such that the ultrasonic transducer is spaced above the planar face of the housing; and
   the apparatus further comprises a lubricant disposed on the planar face of the housing, for enhancing the coupling between the ultrasonic transducer and the subject's blood vessel.

5. Apparatus for non-invasively monitoring the pressure within a subject's blood vessel, comprising:
   a housing;
   a pressure transducer carried on the housing and configured to produce a pressure signal indicative of the pressure applied against it;
   a coupling device configured to urge the housing into compressive engagement with the tissue overlying a subject's blood vessel, to compress the vessel and ensure that pressure variations within the vessel are coupled through the tissue to the pressure transducer; and
   a blood vessel sensor carried on the housing and configured to detect the presence of the blood vessel in the space adjacent to the housing, whereby the apparatus can be moved to place the pressure transducer is in a prescribed position overlying the subject's blood vessel;
   wherein the housing is configured to carry the pressure transducer and the blood vessel sensor in positions such that the space adjacent to the housing in which the blood vessel sensor detects the blood vessel is directly aligned with the space adjacent to the pressure transducer.

6. Apparatus for non-invasively monitoring the pressure within a subject's blood vessel, comprising:
   a housing having at least one inner rigid portion an outer, compliant portion that encircles the at least one inner rigid portion;
   a pressure transducer carried on the housing and configured to produce a pressure signal indicative of the pressure applied against it;
   a coupling device configured to urge the housing into compressive engagement with the tissue overlying a subject's blood vessel, to compress the vessel and ensure that pressure variations within the vessel are coupled through the tissue to the pressure transducer; and a blood vessel sensor carried on the housing and configured to detect the presence of the blood vessel in the space adjacent to the housing, whereby the apparatus can be moved to place the pressure transducer is in a prescribed position overlying the subject's blood vessel;

wherein the at least one rigid portion of the housing carries the pressure transducer and the blood vessel sensor, and the inner and outer portions cooperate to define a substantially planar face configured to compressively engage the tissue overlying the subject's blood vessel.

7. Apparatus for non-invasively monitoring the pressure within a subject's blood vessel, comprising:

a housing;

a pressure transducer carried on the housing and configured to produce a pressure signal indicative of the pressure applied against it;

a coupling device configured to urge the housing into compressive engagement with the tissue overlying a subject's blood vessel, to compress the vessel and ensure that pressure variations within the vessel are coupled through the tissue to the pressure transducer; and a plurality of blood vessel sensors carried on the housing, the plurality of sensors being disposed in an array and configured to detect the presence of the blood vessel in the space adjacent to the housing, the array further being configured to determine a direction to move the apparatus to place the pressure transducer is in a prescribed position overlying the subject's blood vessel.

8. Apparatus as defined in claim 7, and farther comprising:

an adjustment mechanism configured to adjust the position of the pressure transducer toward a prescribed position overlying the subject's blood vessel; and a controller configured to control the adjustment mechanism.

9. Apparatus for non-invasively monitoring the pressure within a subject's blood vessel, comprising:

a housing;

a pressure transducer carried on the housing and configured to produce a pressure signal indicative of the pressure applied against it;

an adjustment mechanism configured to adjust the position of the pressure transducer;

a coupling device configured to urge the housing into compressive engagement with the tissue overlying a subject's blood vessel, to compress the vessel and ensure that pressure variations within the vessel are coupled through the tissue to the pressure transducer; and a blood vessel sensor carried on the housing and configured to detect the presence of the blood vessel in the space adjacent to the housing, whereby the adjustment mechanism and apparatus can be utilized to place the pressure transducer is in a prescribed position overlying the subject's blood vessel.

10. A method for non-invasively monitoring the pressure within a subject's blood vessel, comprising the steps of:

providing a pressure sensing apparatus that includes:
(i) a housing having a substantially planar face configured to compressively engage the tissue overlying the subject's blood vessel, the housing further including a chamber and a recess;
(ii) a pressure transducer carried on the housing and sized to be received within the chamber of the housing, the pressure transducer being configured to produce a pressure signal indicative of the pressure applied against it; and
(iii) a blood vessel sensor carried on the housing and sized to be received within the recess of the housing, the blood vessel sensor being configured to produce a signal indicative of the presence of a vessel in the space adjacent to the housing;

controllably moving the housing across the tissue near a subject's blood vessel until the signal produced by the blood vessel sensor indicates that the housing has reached a prescribed position overlying the subject's blood vessel, the housing being oriented such that an axis connecting its chamber and its recess is substantially parallel with the subject's blood vessel; and urging the housing into compressive engagement with the tissue overlying a subject's blood vessel, to compress the vessel and ensure that pressure variations within the vessel are coupled through the tissue to the pressure transducer carried on the housing.

11. A method for non-invasively monitoring the pressure within a subject's blood vessel, comprising the steps of:

providing a pressure sensing apparatus that includes a housing having a planar face, a pressure transducer carried on the housing and configured to produce a pressure signal indicative of the pressure applied against it, and an ultrasonic transducer carried on the housing and spaced above the planar face thereof, the ultrasonic transducer being configured to produce a signal indicative of the presence of a vessel in the space adjacent to the housing;

placing a lubricant on at least a portion of the planar face of the housing, thereby enhancing the coupling between the ultrasonic transducer and the subject's blood vessel;

controllably moving the housing across the tissue near a subject's blood vessel until the signal produced by the blood vessel sensor indicates that the housing has reached a prescribed position overlying the subject's blood vessel; and urging the housing into compressive engagement with the tissue overlying a subject's blood vessel, to compress the vessel and ensure that pressure variations within the vessel are coupled through the tissue to the pressure transducer carried on the housing.

12. A method for non-invasively monitoring the pressure within a subject's blood vessel, comprising the steps of:

providing a pressure sensing apparatus that includes:
(i) a housing forming a compression surface;
(ii) a pressure transducer having a compression surface and being carried on the housing such that the compression surfaces of the pressure transducer and housing are flush, the pressure transducer further being configured to produce a pressure signal indicative of the pressure applied against it; and
(iii) a blood vessel sensor carried on the housing and configured to produce a signal indicative of the presence of a vessel in the space adjacent to the housing;

controllably moving the housing across the tissue near a subject's blood vessel until the signal produced by the blood vessel sensor indicates that the housing has reached a prescribed position overlying the subject's blood vessel; and urging the compression surface of the housing and the pressure transducer into compressive association with first and second portions of the tissue overlying a subject's blood vessel, respectively, the first portion surrounding the second portion, to compress the vessel and ensure that pressure variations within the vessel are coupled through the tissue to the pressure transducer carried on the housing.

13. A method as defined in claim 12, wherein, in the step of providing, the compression surface of the housing includes an inner section and an outer section, the outer section surrounding the inner section, and the outer section being more compliant that the inner section.

14. A method as defined in claim 12, wherein, in the step of providing, the shape of the compression surface of the housing is longer than it is wide, and in the step of urging, the shape is oriented relative to the blood vessel such that the vessel runs in the compression surface's long direction.

* * * * *